United States Patent
Cho et al.

[11] Patent Number: 5,981,241
[45] Date of Patent: Nov. 9, 1999

[54] METHOD OF PRODUCING ERYTHRITOL

[75] Inventors: Hiroshi Cho; Kenji Yamagishi, both of Yokohama; Shuichi Abe, Kitakyushu; Satoshi Morioka, Yokohama, all of Japan

[73] Assignee: Mitsubishi Chemical Corporation, Tokyo, Japan

[21] Appl. No.: 09/205,286

[22] Filed: Dec. 4, 1998

[30] Foreign Application Priority Data

Dec. 4, 1997 [JP] Japan ................................. 9-334655

[51] Int. Cl.$^6$ ................................................. C12P 7/04
[52] U.S. Cl. ........................ 435/157; 435/171; 435/911; 435/917
[58] Field of Search ..................... 435/157, 917, 435/911, 171

[56] References Cited

FOREIGN PATENT DOCUMENTS

| 0 136 803 | 4/1985 | European Pat. Off. . |
| 0 327 342 | 8/1989 | European Pat. Off. . |
| 47-41549 | 10/1972 | Japan . |
| 51-21072 | 6/1976 | Japan . |

OTHER PUBLICATIONS

Chemical Abstracts, vol. 128, No. 13, Mar. 30, 1998, Columbus, Ohio, US, Abstract No. 153198, Chang, C.C. et al.: "Isolation of an erythritol–producing yeast and studies on its culture conditions".

Chemical Abstracts, vol. 124, No. 6, Feb. 5, 1996, Columbus, Ohio, US, Abstract No. 67527, Schoellner, R. et al.: "Complex formation of straight–chain polyols in aqueous solution with incompletely hydrated K+and Ca2 + cations on X and Y zeolites".

Biosis Computer Abstract 1998:176259 Chang et al "Isolation of an Erythritol–Producing Yeast and Studies on its Culture Conditions" "Report of the Taiwan Sugar Research Inst" Mar. 1997, vol. 0 No. 155, pp.55–67.

Biosis Computer Abstract 1995:219598 Gutierrez–Rojas et al "Citric Acid and Olyols Production by Aspergilus Niger at High Glucose Concentration in Solid State Fermentation of Inert Support" Biotech Letters (1995) vol. 17, No. 2, pp. 219–224.

Caplus Computer Abstract 1990:476512 Bisping et al "Formation of Polyols by Immobillized Microorganisms" Kdechema Biotechno. Conf. (1998) 3 Pt A pp. 511–514, 1989.

*Primary Examiner*—Herbert J. Lilling
*Attorney, Agent, or Firm*—Wenderoth, Lind & Ponack, L.L.P.

[57] ABSTRACT

A method of producing erythritol is disclosed, in which a microorganism having an ability of producing erythritol is cultivated for generation in a medium containing preferably 5 ppm or more of calcium, and erythritol is collected from the culture, thus producing erythritol efficiently.

3 Claims, No Drawings

METHOD OF PRODUCING ERYTHRITOL

BACKGROUND OF THE INVENTION

1. Field of the Invention

The present invention relates to a method of producing erythritol and more particularly to a method of producing erythritol that uses fermentation in a medium containing calcium and produces erythritol in an industrially advantageous manner.

2. Description of the Related Art

In methods of producing erythritol, there have been known a method in which the production is made by cultivating a yeast belonging to the genus Trigonopsis or the genus Candida in a medium containing glycerol as a carbon source and a casein hydrolysate as a nitrogen source (Japanese Examined Patent Publication No. Sho 47-41549), a method in which the production is made by cultivating a yeast belonging to the genus Candida, the genus Torulopsis, or the genus Hansenula in a medium containing a hydrocarbon or the like as a carbon source and yeast extracts or urea as a nitrogen source (Japanese Examined Patent Publication No. Sho 51-21072), and the like. However, these methods have not been yet industrialized since the raw materials used as the carbon source are unsuitable for practical productions on an industrial scale.

Also, there have been known a method in which the production is made by cultivating *Moniliella tomentosa* var *pollinis* in a medium containing a saccharide such as glucose as a carbon source (Japanese Laid-Open Patent Publication No. Sho 60-110295 and the like) and a method in which an erythritol-producing microorganism is cultivated in a medium containing yeast extracts and corn steep liquor as a nitrogen source (Japanese Laid-Open Patent Publication No. Hei 01-199584.

As the method of producing erythritol have been known various methods such as those described above. However, such known methods suffer much load on production process since glycerol is by-produced in large amounts or completion of fermentation (consumption of glucose) takes a long time, and are also economically disadvantageous.

SUMMARY OF THE INVENTION

The present invention is made in view of obviating the above-described problems and is contemplated to provide a method of efficiently producing erythritol using a medium suitable for its production by fermentation on an industrial scale.

As a result of intensive research dedicated to solve the above problems, the present inventors have now found that addition of calcium in a fermentation medium enables one to efficiently produce erythritol using an inexpensive medium. The present invention has been completed based on this discovery.

Accordingly, the present invention provides a method of producing erythritol comprising the steps of: cultivating a microorganism having an ability of producing erythritol in a medium containing calcium; producing erythritol in the medium and collecting erythritol from a culture.

According to a preferred embodiment of the present invention, the method illustrated above wherein the medium contains 5 ppm or more of calcium, and the method illustrated above wherein the microorganism is selected from microorganisms belonging to the genus Moniliella or the genus Trichosporonoides.

DESCRIPTION OF THE PREFERRED EMBODIMENTS

Hereafter, the present invention will be further described in detail.

The microorganism that can be used in the present invention may be any microorganism that have an ability of producing erythritol from a fermentable saccharide and may not be limited to particular ones. More specifically, there are enumerated microorganisms that belong to the genus Moniliella or the genus Trichosporonoides.

Examples of the microorganism that belongs to the genus Moniliella include *Moniliella pollinis*, *Moniliella acetoabutens*, and *Moniliella suaveolents*.

Among them, preferred strains include, for example, *Moniliella pollinis* CBS461.67, *Moniliella pollinis* MCI3554 (FERM BP-6170), *Moniliella acetoabutens* CBS170.66, *Moniliella suaveolens* var *nigra* CBS223.32, *Moniliella suaveolens* var *nigra* CBS382.36, *Moniliella suaveolens* var *nigra* CBS223.79, and the like.

Examples of the microorganism that belongs to the genus Trichosporonoides include *Trichosporonoides oedocephalis*, *Trichosporonoides megachiliensis*, *Trichosporonoides spathulata*, *Trichosporonoides nigrescens*, and *Trichosporonoides madida*.

Among them, preferred strains include, for example, *Trichosporonoides oedocephalis* CBS649.66, *Trichosporonoides oedocephalis* CBS568.85, *Trichosporonoides megachiliensis* CBS567.85, *Trichosporonoides megachiliensis* ATCC76718, *Trichosporonoides megachiliensis* SN-r96 (FERM BP-1431), *Trichosporonoides madida* CBS240.79, *Trichosporonoides nigrescens* CBS268.81, *Trichosporonoides nigrescens* CBS269.81, *Trichosporonoides spathulata* CBS241.79, *Trichosporonoides spathulata* CBS242.79A, *Trichosporonoides spathulata* CBS242.79B, and the like.

These strains have been deposited at Central Bureau voor Schimmelcultures (CBS) in Holland, American Type Culture Collection (ATCC) in U.S.A, and National Institute of Bioscience and Human-Technology of Agency of Industrial Science and Technology, Ministry of International Trade and Industry, in Japan, which are international depository authority and are readily available to one skilled in the art.

In the present invention, there can also be used mutants of these microorganisms obtained by spontaneous mutation or artificial mutation. As the method of mutation treatment, there can be cited usually used methods known per se, for example, such as irradiation of ultraviolet rays, irradiation of X-rays, radiation exposure, a treatment with a mutagen such as N-methyl-N'-nitro-nitrosoguanidine (NTG), artificial mutational treatments such as gene recombination and cell fusion, and the like.

Specific examples of the strain of microorganism that can be used in the present invention include *Moniliella pollinis* MCI3371 strain and *Trichosporonoides megachiliensis* MCI3369 strain.

Among the above strains, MCI3369 strain is a mutant of the strain deposited at Central Bureau voor Schimmelcultures (CBS) as *Trichosporonoides megachiliensis* CBS567.85. The mutant has been obtained by incubating the CBS567.85 strain in a medium containing 30% of glucose and 1.5% of yeast extracts at 30° C. for 2 days, collecting microbial cells, washing the cells twice with physiological saline, treating the washed cells with physiological saline containing 500 to 1,000 μg/ml of NTG (N-methyl-N'-nitro-N-nitrosoguanidine) at 30° C. for 60 minutes to cause mutation, collecting the treated cells, suspending the cells in a medium, incubating the suspension at 30° C. to stabilize the mutation, spreading the cells on an agar medium having the same composition as the liquid medium to allow colony formation, and selecting a colony that does not form foams.

MCI3371 strain is a mutant obtained from the strain deposited at Central Bureau voor Schimmelcultures (CBS) in Holland as *Moniliella pollinis* CBS461.67 by the same mutation treatment as described above.

MCI3369 and MCI3371 strains had been deposited in National Institute of Bioscience and Human-Technology of Agency of Industrial Science and Technology of Ministry of International Trade and Industry (1–3, Higashi 1-chome, Tsukuba-shi, Ibaraki-ken, zip code 305-8566, Japan) on Nov. 28, 1996 under accession numbers FERM P-15967 and FERM P-15969, and then they were transferred to the international deposition based on Budapest Treaty on Nov. 19, 1997 and have been deposited under accession numbers FERM BP-6172 and FERM BP-6173, respectively. MCI3369 and MCI3371 strains have the following mycological properties.

[MCI3369]

MCI3369 strain after cultivation on PDA (potato dextrose agar) at 24° C. appeared at first white, and was turned afterward olive gray or in the case of older cultures of 2 weeks or more it was turned olive brown. The fungus grew rapidly and proliferated by yeast-like budding. The yeast-like cells were colorless at first and then were turned olive brown. Vegetative hyphae, which developed well, with septa and branches, had a width of 2 to 3.8 $\mu$m, were at first colorless, and afterwards had slightly thickened membrane and turned brown. Development of aerial hyphae was excellent and budding-type conidia were formed on the side of aerial hyphae. Vegetative hyphae and aerial hyphae were cut into fragments to form arthrospore-like conidia. The arthrospores were cylindrical or barrel-form (3.6 to 25 $\mu$m×2.2 to 4.3 $\mu$m), at first colorless and turned pale brown afterwards. The budding-type conidia were single or made a chain consisting of 3 to 4 conidia. The conidia were of an oblong ellipse, with a size of 3.4 to 7.5 $\mu$m×1.9 to 4.1 $\mu$m (average 6.5±1.2 $\mu$m×3.8±0.6 $\mu$m) and appeared at first colorless and turned olive brown afterwards.

The morphological properties of the instant strain (MCI3369) well coincided with the characteristics of the type strain of *Trichosporonoides megachiliensis*, CBS567.85, a parent strain of MCI3369. Therefore, this strain was identified as *Trichosporonoides megachiliensis*.

[MCI3371]

MCI3371 strain after cultivation on PDA (potato dextrose agar) at 24° C. appeared at first white to yellowish white, and was turned dull yellow after cultivation for 1 week or blackish brown in the case of older cultures. The fungus grew rapidly and proliferated by yeast-like budding. The budding cells at first had a thin membrane and appeared olive brown and afterwards had a thickened membrane and colored. Simultaneously with the yeast-like budding, vegetative hyphae elongated. The vegetative hyphae had septa and branched. They had a width of 2 to 4.5 $\mu$m, were at first colorless and turned brown afterwards. The hyphae were cut into fragments to form arthrospore-like conidia or budding-type conidia were formed on the side or top of the hypha. The arthrospores were cylindrical or barrel-form (6 to 35 $\mu$m×2.5 to 5.0 $\mu$m), at first colorless and turned pale brown afterwards. The budding-type conidia were single or made a chain consisting of 2 to 3 conidia. The conidia were oval to elliptical, or spheroidal, with a size of 4.7 to 9.4 $\mu$m×3.1 to 5.6 $\mu$m (average 6.8±1.3 $\mu$m×4.5±0.6 $\mu$m) and appeared at first colorless and were turned olive brown afterwards.

The strain (MCI3371) had characteristics that it had a dimorphism, i.e., arthrospore and budding-type conidium, and that the budding-type conidia were formed acropetally but not synchronously. Based on these characteristics, retrieval of genera was conducted according to the monograph of De Hoog & Hermanides-Nijhof (1977), which confirmed that the instant strain belonged to the genus Moniliella. According to De Hoog, "The Black yeasts, II: Moniliella and Allied Genera", Studies in Mycology No. 19, 1–90 (1979), the genus Moniliella is known to include 3 species and 2 varieties: *Moniliella suaveolens* var *suaveolens*, *Moniliella suaveolens* var *nigra*, *Moniliella acetoabutens*, and *Moniliella pollinis*. These species and varieties are distinguished mainly by the morphological characteristics of budding-type conidia and arthrospores. As a result of detailed study of the morphological properties of the present strain, it was found that this strain well coincided with the description of *Moniliella pollinis*. Therefore, this strain was identified as *Moniliella pollinis*.

In the present invention, cultivation of microorganisms having an ability of producing erythritol from a fermentable saccharide is carried out using a medium containing calcium. Other components than calcium may be selected appropriately depending on the microorganism to be used. Main components usually used are shown below.

As the main carbon source, there can be utilized fermentable saccharides such as glucose, fructose, and glycerol. These may be used alone or in combination. Their concentration is not limited particularly but it is within the ranges where production of erythritol is not inhibited. A preferred concentration is within the ranges of 20 to 60% (W/V).

As the nitrogen source used in the cultivation of microorganisms, there can be used various organic and inorganic nitrogen compounds such as ammonia salts, urea, and corn steep liquor. As the inorganic salt, there can be used various phosphoric acid salts, sulfuric acid salts, and salts of a metal such as magnesium, potassium, manganese, or zinc. Also, as a growth factor, there can be added, if desired, one or more factors that promote the growth of microorganisms, such as vitamins, nucleotides, and amino acids. A suitable amount of commercially available antifoam agent is added to the medium in order to prevent foaming during the cultivation due to the components contained in the medium.

The calcium source to be added in the medium is not limited particularly as far as it is a calcium compound. The calcium source includes, for example, calcium chloride ($CaCl_2$), calcium hydroxide ($Ca(OH)_2$) calcium sulfate ($CaSO_4$).

Also, the calcium source may be calcium contained in the water used for preparing a medium. Specifically, service water that contains calcium may be used for preparing a medium.

In the present invention, it is sufficient that the medium contain calcium in a concentration not smaller than a certain concentration no matter which calcium source is used. The concentration of calcium is preferably 5 ppm or more, and more preferably 30 ppm or more. There is no particular upper limit for the calcium concentration. However, usually the amount of erythritol produced is saturated when the calcium concentration exceeds a certain concentration so that it is unnecessary to add calcium to above such a concentration. The calcium concentration at which yield of erythritol is saturated or preferred calcium concentration can be determined by preparing a plurality of media differing in calcium concentration, cultivating in these media a microorganism having an ability of producing erythritol, and measuring the amount of erythritol produced in each medium.

Upon cultivation, microbial cells may be inoculated to a main medium directly from a slant culture. However, it is preferred to inoculate a preculture obtained by cultivation in a liquid medium for 1 to 4 days to the main medium.

The cultivation condition can be appropriately set depending upon the microorganism used. However, in the case where the microorganism belonging to the genus Moniliella or the genus Trichosporonoides is used, such a condition as shown as below may be presented by way of example.

The pH of a medium at initial stage of cultivation is usually pH 3 to 7, preferably pH 3 to 4.5. In the case of pH adjustable cultivation, it is desirable that pH be adjusted to 3 to 4.5 with an acid or alkali during incubation. The incubation temperature is suitably 25 to 37° C., preferably 27 to 37° C. It is preferred that the cultivation be run under aerobic conditions such as aeration, stirring, or shaking.

The cultivation time preferably lasts until the main carbon source(s) is or are consumed and usually the cultivation is continued for 3 to 8 days.

The amount of erythritol thus produced in the culture medium can be determined by a known method usually used such as gas chromatography, or high performance liquid chromatography.

The erythritol that accumulated in the culture medium is separated from the culture and purified in a conventional manner. More specifically, the separation and purification can be carried out by removing solids by centrifugation, filtration or the like, decolorizing and desalting the residual solution with activated carbon or ion exchange resin, and crystallize erythritol from the solution.

According to the method of the present invention, not only erythritol can be produced efficiently by the use of service water, which is an inexpensive raw material, but also there can be constructed industrially advantageous processes that allow for a reduction in purification cost due to a decrease in the occurrence of byproducts such as glycerol and further a reduction in cultivation time.

Hereafter, the present invention will be described in more detail by Examples. However, the present invention is not limited to the methods described below.

The media used in the Examples and Comparative Examples below are as shown in following Tables 1 and 2.

TABLE 1

| Component | Content (%) |
|---|---|
| Glucose | 30 |
| Corn steep liquor | 0.75 |
| Ammonium sulfate | 0.04 |
| Urea | 0.42 |
| Potassium dihydrogen phosphate | 0.08 |
| Thiamine hydrochloride | 0.005 |

TABLE 2

| Component | Content (%) |
|---|---|
| Glucose | 40 |
| Corn steep liquor | 1.5 |
| Ammonium sulfate | 0.886 |
| Potassium dihydrogen phosphate | 0.1 |
| Thiamine hydrochloride | 0.005 |
| Antifoam agent | 0.05 |

EXAMPLE 1

A 200 ml Erlenmeyer flask charged with 20 ml of a liquid medium containing 30% (W/V) of glucose and 1% of yeast extracts (manufactured by Asahi Beer Co., Ltd.) with a cotton plug was sterilized at 120° C. for 20 minutes and a loopful of *Moniliella pollinis* MCI3371 strain that had been slant cultivated by a conventional method was inoculated thereto, followed by incubation with shaking at 35° C. for 3 days.

In a 200 ml baffled flask containing 20 ml of the medium of the above-described composition was added calcium chloride dihydrate ($CaCl_2.2H_2O$) to a calcium concentration of 5 ppm, 15 ppm, 30 ppm, 60 ppm or 120 ppm. Then, 0.5 ml of a seed culture was inoculated and incubated with shaking at 35° C. and 240 rpm for 4 days. As comparison, cultivation was conducted in the same medium without addition of calcium. The concentrations of erythritol (hereafter sometimes abbreviated as "ERT") and glycerol (hereafter sometimes abbreviated as "GLY") in the culture medium were measured by high performance liquid chromatography. The results are shown in Table 3.

TABLE 3

| Calcium Concentration (ppm) | ERT (g/l) | GLY (g/l) |
|---|---|---|
| 0 | 123.7 | 24.5 |
| 5 | 137.0 | 16.3 |
| 15 | 132.5 | 12.1 |
| 30 | 135.5 | 11.4 |
| 60 | 147.0 | 7.7 |
| 120 | 137.5 | 14.0 |

EXAMPLE 2

Cultivation was conducted in the same manner as in Example 1 except that instead of calcium chloride dihydrate, there was added calcium hydroxide ($Ca(OH)_2$) in the same concentration. The concentrations of ERT and GLY in the culture medium were measured by high performance liquid chromatography. The results are shown in Table 4.

TABLE 4

| Calcium Concentration (ppm) | ERT (g/l) | GLY (g/l) |
|---|---|---|
| 0 | 123.7 | 24.5 |
| 5 | 136.0 | 14.2 |
| 15 | 136.0 | 17.7 |
| 30 | 128.0 | 11.0 |
| 60 | 131.5 | 10.5 |
| 120 | 143.0 | 8.7 |

EXAMPLE 3

A 200 ml Erlenmeyer flask charged with 20 ml of a liquid medium containing 30% (W/V) of glucose and 1% of yeast extracts (manufactured by Asahi Beer Co., Ltd.) with a cotton plug was sterilized at 120° C. for 20 minutes and a loopful of MCI3369 strain that had been slant cultivated by a conventional method was inoculated thereto, followed by incubation with shaking at 35° C. for 3 days.

In a 200 ml baffled flask containing 20 ml of the medium of the above-described composition was added calcium chloride dihydrate ($CaCl_2.2H_2O$) to a calcium concentration of .5 ppm, 15 ppm, 30 ppm, 60 ppm or 120 ppm. Then, 0.5 ml of a seed culture was inoculated and incubated with shaking at 35° C. and 240 rpm for 4 days. As comparison, cultivation was conducted in the same medium without addition of calcium. The concentrations of ERT and GLY in the culture medium were measured by high performance liquid chromatography. The results are shown in Table 5.

TABLE 5

| Calcium Concentration (ppm) | ERT (g/l) | GLY (g/l) |
| --- | --- | --- |
| 0 | 90.9 | 58.4 |
| 5 | 104.0 | 33.9 |
| 15 | 109.5 | 28.5 |
| 30 | 115.0 | 11.5 |
| 60 | 107.5 | 22.1 |
| 120 | 111.5 | 10.9 |

EXAMPLE 4

Cultivation was conducted in the same manner as in Example 3 except that instead of calcium chloride dihydrate, there was added calcium hydroxide ($Ca(OH)_2$) in the same concentration. The concentrations of ERT and GLY in the culture medium were measured by high performance liquid chromatography. The results are shown in Table 6.

TABLE 6

| Calcium Concentration (ppm) | ERT (g/l) | GLY (g/l) |
| --- | --- | --- |
| 0 | 90.9 | 58.4 |
| 5 | 106.0 | 29.6 |
| 15 | 111.0 | 26.8 |
| 30 | 113.5 | 11.1 |
| 60 | 116.0 | 4.8 |
| 120 | 106.0 | 11.2 |

EXAMPLE 5

A 200 ml Erlenmeyer flask charged with 20 ml of a liquid medium containing 30% (W/V) of glucose and 1% of yeast extracts (manufactured by Asahi Beer Co., Ltd.) with a cotton plug was sterilized at 120° C. for 20 minutes and a loopful of *Trichosporonoides oedocephalis* CBS649.66 strain that had been slant cultivated by a conventional method was inoculated thereto, followed by incubation with shaking at 30° C. for 3 days. In a 200 ml flask containing 20 ml of the medium of the composition shown in Table 1 to which was added calcium chloride dihydrate ($CaCl_2 \cdot 2H_2O$) to a calcium concentration of 15 ppm or 30 ppm. Then, 0.5 ml of a seed culture was inoculated and incubated with shaking at 30° C. and 160 rpm for 4 days. As comparison, cultivation was conducted in the same medium without addition of calcium. The concentrations of ERT and GLY in the culture medium were measured by high performance liquid chromatography. The results are shown in Table 7.

TABLE 7

| Calcium Concentration (ppm) | ERT (g/l) | GLY (g/l) |
| --- | --- | --- |
| 0 | 17.1 | 5.9 |
| 15 | 22.0 | 1.2 |
| 30 | 22.2 | 0 |

EXAMPLE 6

Cultivation was conducted in the same manner as in Example 5 except that instead of CBS649.66 strain, there was used *Trichosporonoides megachiliensis* CBS567.85.

The concentrations of ERT and GLY in the culture medium were measured by high performance liquid chromatography. The results are shown in Table 8.

TABLE 8

| Calcium Concentration (ppm) | ERT (g/l) | GLY (g/l) |
| --- | --- | --- |
| 0 | 21.8 | 4.5 |
| 15 | 25.2 | 0 |
| 30 | 23.9 | 0 |

EXAMPLE 7

Cultivation was conducted in the same manner as in Example 5 except that instead of CBS649.66 strain, there was used *Trichosporonoides nigrescens* CBS268.81. The concentrations of ERT and GLY in the culture medium were measured by high performance liquid chromatography. The results are shown in Table 9.

TABLE 9

| Calcium Concentration (ppm) | ERT (g/l) | GLY (g/l) |
| --- | --- | --- |
| 0 | 44.2 | 18.3 |
| 15 | 53.8 | 1.7 |
| 30 | 52.9 | 2.9 |

EXAMPLE 8

A 200 ml Erlenmeyer flask charged with 20 ml of a liquid medium containing 30% (W/V) of glucose and 1% of yeast extracts (manufactured by Asahi Beer Co., Ltd.) with a cotton plug was sterilized at 120° C. for 20 minutes and a loopful of *Trichosporonoides megachiliensis* MCI3369 strain that had been slant cultivated by a conventional method was inoculated thereto, followed by incubation with shaking at 35° C. for 3 days. Media having the composition shown in Table 1 were prepared using deionized water and service water (containing 18 ppm of calcium), respectively, and were poured by 20 ml in 200 ml baffled flasks, respectively. To each of them was inoculated 0.5 ml of the thus obtained seed culture and incubated with shaking at 35° C. and 240 rpm for 4 days. The results are shown in Table 10.

TABLE 10

| Medium | ERT (g/l) | GLY (g/l) |
| --- | --- | --- |
| Medium with deionized water | 58.5 | 57.5 |
| Medium with service water | 71.8 | 36.2 |

EXAMPLE 9

A 200 ml Erlenmeyer flask charged with 20 ml of a liquid medium containing 30% (W/V) of glucose and 1% of yeast extracts (manufactured by Asahi Beer Co., Ltd.) with a cotton plug was sterilized at 120° C. for 20 minutes and a loopful of e *Moniliella pollinis* MIC3371 strain that had been slant cultivated by a conventional method was inoculated thereto, followed by incubation with shaking at 35° C. for 3 days. Then, to a medium having the composition shown in Table 2 was added calcium chloride dihydrate (CaCl₂.2H₂O) to a calcium concentration of 30 ppm, and 600 ml portion of the medium was introduced into a 1 liter of fermentation tank. Then, 10 ml of the above-described seed culture was inoculated in the fermentation tank, followed by incubation under the conditions of 35° C., an air flow rate of 0.5 vvm, and a rotation number of 800 rpm for 4 days. During the cultivation, the pH of the medium was controlled to 3.8 to 4.0 with 5 N sodium hydroxide (NaOH. The concentrations of glucose (hereafter sometimes abbreviated as "GLU"), ERT and GLY in the culture medium were measured by high performance liquid chromatography. The results are shown in Table 11.

TABLE 11

| Incubation Time (Hr) | GLU (g/l) | ERT (g/l) | GLY (g/l) |
| --- | --- | --- | --- |
| 93 | 0 | 180.8 | 18.6 |

COMPARATIVE EXAMPLE 1

Cultivation was conducted under the same conditions as in Example 9 except that no calcium was added to the medium. The concentrations of GLU, ERT and GLY in the culture medium were measured by high performance liquid chromatography. The results are shown in Table 12.

TABLE 12

| Incubation Time (Hr) | GLU (g/l) | ERT (g/l) | GLY (g/l) |
| --- | --- | --- | --- |
| 93 | 35.3 | 132.7 | 61.7 |

EXAMPLE 10

A 200 ml Erlenmeyer flask charged with 20 ml of a liquid medium containing 30% (W/V) of glucose and 1% of yeast extracts (manufactured by Asahi Beer Co., Ltd.) with a cotton plug was sterilized at 120° C. for 20 minutes and a loopful of *Trichosporonoides megachiliensis* CBS567.85 strain that had been slant cultivated by a conventional method was inoculated thereto, followed by incubation at 35° C. for 3 days. Then, to a medium having the composition shown in Table 2 was prepared using service water (containing 18 ppm of calcium) and 600 ml portion of the medium was introduced into a 1 liter of fermentation tank. Then, 10 ml of the above-described seed culture was inoculated in the fermentation tank, followed by incubation under the conditions of 35° C., an air flow rate of 0.5 vvm, and a rota-ion number of 800 rpm for 4 days. During the incubation, the pH of the medium was controlled to 3.8 to 4.0 with 5 N sodium hydroxide (NaOH). The concentrations of GLU, ERT and GLY during the incubation were measured by high performance liquid chromatography. The results are shown in Table 13.

TABLE 13

| Incubation Time (Hr) | GLU (g/l) | ERT (g/l) | GLY (g/l) |
| --- | --- | --- | --- |
| 92 | 0 | 150.5 | 63.4 |

COMPARATVE EXAMPLE 2

Cultivation was conducted under the same conditions as in Example 10 except that instead of service water, there was used deionized water. The concentrations of GLU, ERT and GLY during the incubation were measured by high performance liquid chromatography. The results are shown in Table 14.

TABLE 14

| Incubation Time (Hr) | GLU (g/l) | ERT (g/l) | GLY (g/l) |
| --- | --- | --- | --- |
| 92 | 12.7 | 136.0 | 76.8 |

EXAMPLE 11

Cultivation was conducted under the same conditions as in Example 5 except that *Trichosporonoides madida* CBS240.79 was used. The concentrations of ERT and GLY in the culture medium were measured. The results are shown in Table 15.

TABLE 15

| Calcium Concentration (ppm) | ERT (g/l) | GLY (g/l) |
| --- | --- | --- |
| 0 | 18.3 | 43.2 |
| 15 | 11.2 | 0 |
| 30 | 12.4 | 0 |

EXAMPLE 12

Cultivation was conducted under the same conditions as in Example 5 except that *Moniliealla suaveolens* var *nigra* CBS223.79 was used and a concentration of glucose in the medium shown in Table 1 was 20%(W/V). The concentrations of ERT and GLY in the culture medium were measured. The results are shown in Table 16.

TABLE 16

| Calcium Concentration (ppm) | ERT (g/l) | GLY (g/l) |
| --- | --- | --- |
| 0 | 4.2 | 5.1 |
| 15 | 5.8 | 0 |
| 30 | 6.4 | 0 |

EXAMPLE 13

Cultivation was conducted under the same conditions as in Example 5 except that *Trichosporonoides megachiliensis* SN-r96 (FERM BP-1431) was used and a concentration of glucose in the medium shown in Table 1 was 20% (W/V). The concentrations of ERT and GLY in the culture medium were measured. The results are shown in Table 17.

TABLE 17

| Calcium Concentration (ppm) | ERT (g/l) | GLY (g/l) |
|---|---|---|
| 0 | 67.5 | 5.6 |
| 15 | 68.5 | 3.3 |
| 30 | 67.8 | 1.0 |

EXAMPLE 14

Cultivation was conducted under the same conditions as in Example 5 except that *Trichosporonoides spathulata* CBS241.81 was used. The concentrations of ERT and GLY in the culture medium were measured. The results are shown in Table 18.

TABLE 18

| Calcium Concentration (ppm) | ERT (g/l) | GLY (g/l) |
|---|---|---|
| 0 | 21.2 | 3.9 |
| 15 | 23.4 | 1.6 |
| 30 | 24 | 1.6 |

EXAMPLE 15

Cultivation was conducted under the same conditions as in Example 5 except that *Moniliella acetoabutens* CBS170.66 was used. The concentrations of ERT and GLY in the culture medium were measured. The results are shown in Table 19.

TABLE 19

| Calcium Concentration (ppm) | ERT (g/l) | GLY (g/l) |
|---|---|---|
| 0 | 1.2 | 19.5 |
| 15 | 10.2 | 10.6 |
| 30 | 11.1 | 10.3 |

What is claimed is:

1. A method of producing erythritol, comprising:

cultivating a microorganism belonging to the genera Moniliella or Trichosporonoides which produces erythritol in a medium containing calcium ranging in concentration from about 5 ppm to about 120 ppm, and collecting erythritol from the culture.

2. The method as claimed in claim 1, wherein said microorganism belonging to the genus Moniliella is selected from the group consisting of *Moniliella pollinis, Moniliella acetoabutens*, and *Moniliella suaveolents*.

3. The method as claimed in claim 1, wherein said microorganism belonging to the genus Trichosporonoides is selected from the group consisting of *Trichosporonoides oedocepharis, Trichosporonoides megachiliensis, Trichosporonoides spathulata, Trichosporonoides nigrescens*, and *Trichosporonoides madida*.

\* \* \* \* \*